(12) United States Patent
Beidler et al.

(10) Patent No.: US 7,872,102 B2
(45) Date of Patent: Jan. 18, 2011

(54) ANTI-IL-23 ANTIBODIES

(75) Inventors: Catherine Brautigam Beidler, Poway, CA (US); Stuart Willis Bright, Carmel (IN); Craig Duane Dickinson, San Diego, CA (US); Kristine Kay Kikly, Fortville (IN); David Matthew Marquis, Encinitas, CA (US); Alain Philippe Vasserot, Carlsbad, CA (US)

(73) Assignee: Eli Lilly and Company, Indianapolis, IN (US)

( * ) Notice: Subject to any disclaimer, the term of this patent is extended or adjusted under 35 U.S.C. 154(b) by 324 days.

(21) Appl. No.: 11/997,597

(22) PCT Filed: Aug. 23, 2006

(86) PCT No.: PCT/US2006/032752

§ 371 (c)(1),
(2), (4) Date: Feb. 1, 2008

(87) PCT Pub. No.: WO2007/024846

PCT Pub. Date: Mar. 1, 2007

(65) Prior Publication Data

US 2009/0240036 A1    Sep. 24, 2009

Related U.S. Application Data

(60) Provisional application No. 60/711,336, filed on Aug. 25, 2005, provisional application No. 60/772,355, filed on Feb. 10, 2006.

(51) Int. Cl.
*C12P 21/08* (2006.01)
*C07K 16/00* (2006.01)
*A61K 39/395* (2006.01)
*C12P 21/04* (2006.01)

(52) U.S. Cl. ............ 530/387.3; 530/388.1; 530/388.23; 424/133.1; 424/141.1; 424/145.1; 435/69.6; 435/70.21

(58) Field of Classification Search ....................... None
See application file for complete search history.

(56) References Cited

U.S. PATENT DOCUMENTS 6,060,284 A    5/2000    Bazan
6,610,285 B1   8/2003    Hirata

FOREIGN PATENT DOCUMENTS

WO    WO 01/18051    3/2001

*Primary Examiner*—David J. Blanchard
(74) *Attorney, Agent, or Firm*—Andrea M. Castetter

(57) ABSTRACT

The present invention encompasses isolated antibodies, or antigen-binding portions thereof, that specifically bind to the p19 subunit of IL-23. These antibodies, or antigen-binding portions thereof, are high affinity, neutralizing antibodies useful for the treatment of autoimmune disease.

3 Claims, No Drawings

SEQUENCE LISTING

<160> NUMBER OF SEQ ID NOS: 65

<210> SEQ ID NO 1
<211> LENGTH: 10
<212> TYPE: PRT
<213> ORGANISM: homo sapiens

<400> SEQUENCE: 1

Gly Lys Thr Phe Thr Ser Tyr Gly Ile Asn
1               5                   10

<210> SEQ ID NO 2
<211> LENGTH: 10
<212> TYPE: PRT
<213> ORGANISM: homo sapiens

<400> SEQUENCE: 2

Gly Lys Thr Phe Phe Ser Tyr Gly Ile Asn
1               5                   10

<210> SEQ ID NO 3
<211> LENGTH: 10
<212> TYPE: PRT
<213> ORGANISM: homo sapiens

<400> SEQUENCE: 3

Gly Lys Thr Phe Trp Ser Tyr Gly Ile Asn
1               5                   10

<210> SEQ ID NO 4
<211> LENGTH: 10
<212> TYPE: PRT
<213> ORGANISM: homo sapiens

<400> SEQUENCE: 4

Gly Lys Thr Phe Tyr Ser Tyr Gly Ile Asn
1               5                   10

<210> SEQ ID NO 5
<211> LENGTH: 17
<212> TYPE: PRT
<213> ORGANISM: homo sapiens

<400> SEQUENCE: 5

Tyr Ile Tyr Ile Gly Asn Gly Tyr Thr Glu Ser Asn Glu Lys Phe Lys
1               5                   10                  15

Gly

<210> SEQ ID NO 6
<211> LENGTH: 17
<212> TYPE: PRT
<213> ORGANISM: homo sapiens

<400> SEQUENCE: 6

Tyr Ile Tyr Ile Gly Gly Gly Tyr Thr Glu Pro Asn Pro Lys Tyr Lys
1               5                   10                  15

Gly

<210> SEQ ID NO 7
<211> LENGTH: 17
<212> TYPE: PRT
<213> ORGANISM: homo sapiens

```
<400> SEQUENCE: 7

Tyr Ile Tyr Ile Gly Asn Gly Tyr Thr Glu Pro Asn Pro Lys Tyr Lys
1               5                   10                  15
Gly

<210> SEQ ID NO 8
<211> LENGTH: 17
<212> TYPE: PRT
<213> ORGANISM: homo sapiens

<400> SEQUENCE: 8

Tyr Ile Tyr Ile Gly Thr Gly Tyr Thr Glu Pro Asn Pro Lys Tyr Lys
1               5                   10                  15
Gly

<210> SEQ ID NO 9
<211> LENGTH: 17
<212> TYPE: PRT
<213> ORGANISM: homo sapiens

<400> SEQUENCE: 9

Tyr Ile Tyr Ile Gly Ser Gly Tyr Thr Glu Pro Asn Pro Lys Tyr Lys
1               5                   10                  15
Gly

<210> SEQ ID NO 10
<211> LENGTH: 17
<212> TYPE: PRT
<213> ORGANISM: homo sapiens

<400> SEQUENCE: 10

Tyr Ile Tyr Ile Gly Arg Gly Tyr Thr Glu Pro Asn Pro Lys Tyr Lys
1               5                   10                  15
Gly

<210> SEQ ID NO 11
<211> LENGTH: 17
<212> TYPE: PRT
<213> ORGANISM: homo sapiens

<400> SEQUENCE: 11

Tyr Ile Tyr Ile Gly Tyr Gly Tyr Thr Glu Pro Asn Pro Lys Tyr Lys
1               5                   10                  15
Gly

<210> SEQ ID NO 12
<211> LENGTH: 10
<212> TYPE: PRT
<213> ORGANISM: homo sapiens

<400> SEQUENCE: 12

Ile Gly Ala Tyr Tyr Gly Asn Phe Asp Tyr
1               5                   10

<210> SEQ ID NO 13
<211> LENGTH: 10
<212> TYPE: PRT
<213> ORGANISM: homo sapiens

<400> SEQUENCE: 13
```

```
Ile Gly Gly Tyr Tyr Gly Asn Phe Thr Asp
1               5                   10

<210> SEQ ID NO 14
<211> LENGTH: 10
<212> TYPE: PRT
<213> ORGANISM: homo sapiens

<400> SEQUENCE: 14

Ile Gly Gly Tyr Tyr Gly Asn Phe Asp Asp
1               5                   10

<210> SEQ ID NO 15
<211> LENGTH: 10
<212> TYPE: PRT
<213> ORGANISM: homo sapiens

<400> SEQUENCE: 15

Ile Gly Gly Tyr Tyr Gly Asn Phe His Asp
1               5                   10

<210> SEQ ID NO 16
<211> LENGTH: 10
<212> TYPE: PRT
<213> ORGANISM: homo sapiens

<400> SEQUENCE: 16

Ile Gly Gly Tyr Tyr Gly Asn Phe Ala Asp
1               5                   10

<210> SEQ ID NO 17
<211> LENGTH: 10
<212> TYPE: PRT
<213> ORGANISM: homo sapiens

<400> SEQUENCE: 17

Ile Gly Gly Tyr Tyr Gly Asn Phe Lys Asp
1               5                   10

<210> SEQ ID NO 18
<211> LENGTH: 10
<212> TYPE: PRT
<213> ORGANISM: homo sapiens

<400> SEQUENCE: 18

Ile Gly Gly Tyr Tyr Gly Asn Phe Asp His
1               5                   10

<210> SEQ ID NO 19
<211> LENGTH: 10
<212> TYPE: PRT
<213> ORGANISM: homo sapiens

<400> SEQUENCE: 19

Ile Gly Gly Tyr Tyr Gly Asn Phe Asp Gln
1               5                   10

<210> SEQ ID NO 20
<211> LENGTH: 10
<212> TYPE: PRT
<213> ORGANISM: homo sapiens

<400> SEQUENCE: 20

Ile Gly Gly Tyr Tyr Gly Asn Phe Gln Asp
1               5                   10
```

```
<210> SEQ ID NO 21
<211> LENGTH: 10
<212> TYPE: PRT
<213> ORGANISM: homo sapiens

<400> SEQUENCE: 21

Ile Gly Gly Tyr Tyr Gly Asn Phe Glu Asp
1               5                   10

<210> SEQ ID NO 22
<211> LENGTH: 10
<212> TYPE: PRT
<213> ORGANISM: homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 22

Gly Lys Thr Phe Xaa Ser Tyr Gly Ile Asn
1               5                   10

<210> SEQ ID NO 23
<211> LENGTH: 17
<212> TYPE: PRT
<213> ORGANISM: homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 23

Tyr Ile Tyr Ile Gly Xaa Gly Tyr Thr Glu Xaa Asn Xaa Lys Xaa Lys
1               5                   10                  15

Gly

<210> SEQ ID NO 24
<211> LENGTH: 10
<212> TYPE: PRT
<213> ORGANISM: homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 24

Ile Gly Xaa Tyr Tyr Gly Asn Phe Xaa Xaa
1               5                   10

<210> SEQ ID NO 25
<211> LENGTH: 16
<212> TYPE: PRT
```

-continued

```
<213> ORGANISM: homo sapiens

<400> SEQUENCE: 25

Lys Ser Ser Gln Ser Leu Leu Asp Ser Asp Gly Lys Thr Tyr Leu Asn
1               5                   10                  15

<210> SEQ ID NO 26
<211> LENGTH: 16
<212> TYPE: PRT
<213> ORGANISM: homo sapiens

<400> SEQUENCE: 26

Gln Ser Ser Gln Ser Leu Leu Ile Ser Gly Gly Asn Thr Tyr Leu Asn
1               5                   10                  15

<210> SEQ ID NO 27
<211> LENGTH: 16
<212> TYPE: PRT
<213> ORGANISM: homo sapiens

<400> SEQUENCE: 27

Gln Ser Ser Gln Ser Leu Leu Ile Ser Gly Gly Lys Thr Tyr Leu Asn
1               5                   10                  15

<210> SEQ ID NO 28
<211> LENGTH: 16
<212> TYPE: PRT
<213> ORGANISM: homo sapiens

<400> SEQUENCE: 28

Arg Ser Ser Gln Ser Leu Leu Ile Ser Gly Gly Asn Thr Tyr Leu Asn
1               5                   10                  15

<210> SEQ ID NO 29
<211> LENGTH: 16
<212> TYPE: PRT
<213> ORGANISM: homo sapiens

<400> SEQUENCE: 29

Arg Ser Ser Gln Ser Leu Leu Ile Ser Gly Gly Lys Thr Tyr Leu Asn
1               5                   10                  15

<210> SEQ ID NO 30
<211> LENGTH: 16
<212> TYPE: PRT
<213> ORGANISM: homo sapiens

<400> SEQUENCE: 30

Lys Ser Ser Gln Ser Leu Leu Ile Ser Gly Gly Asn Thr Tyr Leu Asn
1               5                   10                  15

<210> SEQ ID NO 31
<211> LENGTH: 16
<212> TYPE: PRT
<213> ORGANISM: homo sapiens

<400> SEQUENCE: 31

Lys Ser Ser Gln Ser Leu Leu Ile Ser Gly Gly Lys Thr Tyr Leu Asn
1               5                   10                  15

<210> SEQ ID NO 32
<211> LENGTH: 16
<212> TYPE: PRT
<213> ORGANISM: homo sapiens
```

```
<400> SEQUENCE: 32

Arg Ser Ser Gln Ser Leu Leu Ile Ser Gly Gly Pro Thr Tyr Leu Asn
1               5                   10                  15

<210> SEQ ID NO 33
<211> LENGTH: 16
<212> TYPE: PRT
<213> ORGANISM: homo sapiens

<400> SEQUENCE: 33

Gln Ser Ser Gln Ser Leu Leu Ile Ser Gly Gly Pro Thr Tyr Leu Asn
1               5                   10                  15

<210> SEQ ID NO 34
<211> LENGTH: 16
<212> TYPE: PRT
<213> ORGANISM: homo sapiens

<400> SEQUENCE: 34

Lys Ser Ser Gln Ser Leu Leu Ile Ser Gly Gly Pro Thr Tyr Leu Asn
1               5                   10                  15

<210> SEQ ID NO 35
<211> LENGTH: 16
<212> TYPE: PRT
<213> ORGANISM: homo sapiens

<400> SEQUENCE: 35

Lys Ser Ser Gln Ser Leu Leu Ile Ser Gly Gly Asn Thr Tyr Leu Asn
1               5                   10                  15

<210> SEQ ID NO 36
<211> LENGTH: 7
<212> TYPE: PRT
<213> ORGANISM: homo sapiens

<400> SEQUENCE: 36

Leu Val Ser Lys Leu Asp Ser
1               5

<210> SEQ ID NO 37
<211> LENGTH: 7
<212> TYPE: PRT
<213> ORGANISM: homo sapiens

<400> SEQUENCE: 37

Leu Val Ser Lys Leu Asp Gln
1               5

<210> SEQ ID NO 38
<211> LENGTH: 7
<212> TYPE: PRT
<213> ORGANISM: homo sapiens

<400> SEQUENCE: 38

Lys Val Ser Lys Leu Asp Gln
1               5

<210> SEQ ID NO 39
<211> LENGTH: 9
<212> TYPE: PRT
<213> ORGANISM: homo sapiens

<400> SEQUENCE: 39
```

Trp Gln Gly Thr His Phe Pro Leu Thr
1               5

<210> SEQ ID NO 40
<211> LENGTH: 9
<212> TYPE: PRT
<213> ORGANISM: homo sapiens

<400> SEQUENCE: 40

Trp Gln Gly Thr Tyr Phe Pro Leu Thr
1               5

<210> SEQ ID NO 41
<211> LENGTH: 16
<212> TYPE: PRT
<213> ORGANISM: homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 41

Xaa Ser Ser Gln Ser Leu Leu Xaa Ser Xaa Gly Xaa Thr Tyr Leu Asn
1               5                   10                  15

<210> SEQ ID NO 42
<211> LENGTH: 7
<212> TYPE: PRT
<213> ORGANISM: homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 42

Xaa Val Ser Lys Leu Asp Xaa
1               5

<210> SEQ ID NO 43
<211> LENGTH: 9
<212> TYPE: PRT
<213> ORGANISM: homo sapiens
<220> FEATURE:
<221> NAME/KEY: misc_feature
<222> LOCATION: (5)..(5)
<223> OTHER INFORMATION: Xaa can be any naturally occurring amino acid

<400> SEQUENCE: 43

Trp Gln Gly Thr Xaa Phe Pro Leu Thr
1               5

<210> SEQ ID NO 44
<211> LENGTH: 119
<212> TYPE: PRT

<213> ORGANISM: homo sapiens

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe Thr Asp Trp Gly Gln Gly
            100                 105                 110

Thr Thr Val Thr Val Ser Ser
        115

<210> SEQ ID NO 45
<211> LENGTH: 119
<212> TYPE: PRT
<213> ORGANISM: homo sapiens

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Asn Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe Thr Asp Trp Gly Gln Gly
            100                 105                 110

Thr Thr Val Thr Val Ser Ser
        115

<210> SEQ ID NO 46
<211> LENGTH: 119
<212> TYPE: PRT
<213> ORGANISM: homo sapiens

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Phe Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Asn Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe Thr Asp Trp Gly Gln Gly
            100                 105                 110

Thr Thr Val Thr Val Ser Ser
        115

<210> SEQ ID NO 47
<211> LENGTH: 119
<212> TYPE: PRT
<213> ORGANISM: homo sapiens

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Asn Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe His Asp Trp Gly Gln Gly
            100                 105                 110

Thr Thr Val Thr Val Ser Ser
        115

<210> SEQ ID NO 48
<211> LENGTH: 119
<212> TYPE: PRT
<213> ORGANISM: homo sapiens

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Thr Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe Ala Asp Trp Gly Gln Gly
            100                 105                 110

Thr Thr Val Thr Val Ser Ser
        115

<210> SEQ ID NO 49

```
<211> LENGTH: 119
<212> TYPE: PRT
<213> ORGANISM: homo sapiens

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Ser Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe His Asp Trp Gly Gln Gly
            100                 105                 110

Thr Thr Val Thr Val Ser Ser
        115

<210> SEQ ID NO 50
<211> LENGTH: 119
<212> TYPE: PRT
<213> ORGANISM: homo sapiens

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Thr Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe Lys Asp Trp Gly Gln Gly
            100                 105                 110

Thr Thr Val Thr Val Ser Ser
        115

<210> SEQ ID NO 51
<211> LENGTH: 119
<212> TYPE: PRT
<213> ORGANISM: homo sapiens

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45
```

Gly Tyr Ile Tyr Ile Gly Thr Gly Tyr Thr Glu Pro Asn Pro Lys Tyr
            50                  55                  60

Lys Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Ile Gly Gly Tyr Tyr Gly Asn Phe Asp His Trp Gly Gln Gly
            100                 105                 110

Thr Thr Val Thr Val Ser Ser
        115

<210> SEQ ID NO 52
<211> LENGTH: 119
<212> TYPE: PRT
<213> ORGANISM: homo sapiens

<400> SEQUENCE: 52

Gln Val Gln Leu Val Gln Ser Gly Ala Glu Val Lys Lys Pro Gly Ala
 1               5                  10                  15

Ser Val Lys Val Ser Cys Lys Val Ser Gly Lys Thr Phe Trp Ser Tyr
                 20                  25                  30

Gly Ile Asn Trp Val Arg Gln Ala Pro Gly Lys Gly Leu Glu Trp Met
             35                  40                  45

Gly Tyr Ile Tyr Ile Gly Thr Gly Tyr Thr Glu Pro Asn Pro Lys Tyr
            50                  55                  60

Lys Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Ile Gly Gly Tyr Tyr Gly Asn Phe Asp Gln Trp Gly Gln Gly
            100                 105                 110

Thr Thr Val Thr Val Ser Ser
        115

<210> SEQ ID NO 53
<211> LENGTH: 119
<212> TYPE: PRT
<213> ORGANISM: homo sapiens

<400> SEQUENCE: 53

Gln Val Gln Leu Val Gln Ser Gly Ala Glu Val Lys Lys Pro Gly Ala
 1               5                  10                  15

Ser Val Lys Val Ser Cys Lys Val Ser Gly Lys Thr Phe Trp Ser Tyr
                 20                  25                  30

Gly Ile Asn Trp Val Arg Gln Ala Pro Gly Lys Gly Leu Glu Trp Met
             35                  40                  45

Gly Tyr Ile Tyr Ile Gly Arg Gly Tyr Thr Glu Pro Asn Pro Lys Tyr
            50                  55                  60

Lys Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Ile Gly Gly Tyr Tyr Gly Asn Phe Gln Asp Trp Gly Gln Gly
            100                 105                 110

Thr Thr Val Thr Val Ser Ser
        115

<210> SEQ ID NO 54
<211> LENGTH: 119
<212> TYPE: PRT
<213> ORGANISM: homo sapiens

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Tyr Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe Glu Asp Trp Gly Gln Gly
            100                 105                 110

Thr Thr Val Thr Val Ser Ser
        115

<210> SEQ ID NO 55
<211> LENGTH: 119
<212> TYPE: PRT
<213> ORGANISM: homo sapiens

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Val Ser Gly Lys Thr Phe Trp Ser Tyr
            20                  25                  30

Gly Ile Asn Trp Val Arg Gln Ala Pro Gly Lys Gly Leu Glu Trp Met
        35                  40                  45

Gly Tyr Ile Tyr Ile Gly Thr Gly Tyr Thr Glu Pro Asn Pro Lys Tyr
    50                  55                  60

Lys Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Gly Tyr Tyr Gly Asn Phe Glu Asp Trp Gly Gln Gly
            100                 105                 110

Thr Thr Val Thr Val Ser Ser
        115

<210> SEQ ID NO 56
<211> LENGTH: 112
<212> TYPE: PRT
<213> ORGANISM: homo sapiens

<400> SEQUENCE: 56

Asp Val Val Met Thr Gln Ser Pro Leu Ser Leu Pro Val Thr Leu Gly
1               5                   10                  15

Gln Pro Ala Ser Ile Ser Cys Gln Ser Ser Gln Ser Leu Leu Ile Ser
            20                  25                  30

Gly Gly Lys Thr Tyr Leu Asn Trp Phe Gln Gln Arg Pro Gly Gln Ser

```
            35                  40                  45
Pro Arg Arg Leu Ile Tyr Leu Val Ser Lys Leu Asp Gln Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr Tyr Phe Pro Leu Thr Phe Gly Gln Gly Thr Lys Leu Glu Ile Lys
            100                 105                 110

<210> SEQ ID NO 57
<211> LENGTH: 112
<212> TYPE: PRT
<213> ORGANISM: homo sapiens

<400> SEQUENCE: 57

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Leu Ile Ser
             20                  25                  30

Gly Gly Lys Thr Tyr Leu Asn Trp Phe Gln Gln Arg Pro Gly Gln Ser
         35                  40                  45

Pro Arg Arg Leu Ile Tyr Leu Val Ser Lys Leu Asp Gln Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr Tyr Phe Pro Leu Thr Phe Gly Gln Gly Thr Lys Leu Glu Ile Lys
            100                 105                 110

<210> SEQ ID NO 58
<211> LENGTH: 112
<212> TYPE: PRT
<213> ORGANISM: homo sapiens

<400> SEQUENCE: 58

Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Leu Ile Ser
             20                  25                  30

Gly Gly Pro Thr Tyr Leu Asn Trp Leu Gln Gln Arg Pro Gly Gln Ser
         35                  40                  45

Pro Arg Arg Leu Ile Tyr Lys Val Ser Lys Leu Asp Gln Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr Tyr Phe Pro Leu Thr Phe Gly Gln Gly Thr Lys Leu Glu Ile Lys
            100                 105                 110

<210> SEQ ID NO 59
<211> LENGTH: 112
<212> TYPE: PRT
<213> ORGANISM: homo sapiens

<400> SEQUENCE: 59
```

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Ile Ser
            20                  25                  30

Gly Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Gln Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Tyr Phe Pro Leu Thr Phe Gly Gln Gly Thr Lys Leu Glu Ile Lys
                100                 105                 110
```

<210> SEQ ID NO 60
<211> LENGTH: 189
<212> TYPE: PRT
<213> ORGANISM: homo sapiens

<400> SEQUENCE: 60

```
Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
                100                 105                 110

Pro Ser Leu Leu Pro Asp Ser Pro Val Gly Gln Leu His Ala Ser Leu
                115                 120                 125

Leu Gly Leu Ser Gln Leu Leu Gln Pro Glu Gly His His Trp Glu Thr
            130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 61
<211> LENGTH: 329
<212> TYPE: PRT
<213> ORGANISM: homo sapiens

<400> SEQUENCE: 61

```
Ala Ser Phe Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Glu Trp Glu Thr Trp Arg Arg
        275                 280                 285

Leu Tyr Trp Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 62
<211> LENGTH: 329
<212> TYPE: PRT
<213> ORGANISM: homo sapiens

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                        85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 63
<211> LENGTH: 107
<212> TYPE: PRT
<213> ORGANISM: homo sapiens

<400> SEQUENCE: 63

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Pro Arg Thr Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

```
<210> SEQ ID NO 64
<211> LENGTH: 119
<212> TYPE: PRT
<213> ORGANISM: homo sapiens

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ile Gly Ala Tyr Tyr Gly Asn Phe Asp Tyr Trp Gly Gln Gly
            100                 105                 110

Thr Thr Val Thr Val Ser Ser
        115

<210> SEQ ID NO 65
<211> LENGTH: 112
<212> TYPE: PRT
<213> ORGANISM: homo sapiens

<400> SEQUENCE: 65

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gln Gly Thr Lys Leu Glu Ile Lys
            100                 105                 110
```

ANTI-IL-23 ANTIBODIES

This is the national phase application, under 35 USC 371, for PCT/US2006/032752, filed 23 Aug. 2006, which, claims the benefit, under 35 USC 119(e), of U.S. provisional applications 60/711,336, filed 25 Aug. 2005, and 60/772,355, filed 10 Feb. 2006.

FIELD OF THE INVENTION

The present invention is in the field of medicine, particularly in the field of monoclonal antibodies against interleukin 23 (IL-23). More specifically the invention relates to neutralizing anti-IL-23 monoclonal antibodies for the treatment of autoimmune disease.

BACKGROUND OF THE INVENTION

IL-23 is a cytokine believed to be important for activation of a range of inflammatory cells that are required for the induction of chronic inflammation. IL-23 has a separate but complementary function to IL-12, a heterodimeric cytokine of 70 KDa consisting of covalently linked p40 and p35 subunits. IL-23 is composed of the same p40 subunit as IL-12 but covalently paired with a p19 subunit (Langrish et. al., *Immunological Reviews* 202:96-105, 2004).

Furthermore, IL-23 has been implicated to play an important role in memory/pathogenic T-cell responses by promoting the secretion of the pro-inflammatory cytokine IL-17 from activated T cells. There is increasing evidence that high levels of IL-17 are associated with autoimmune, inflammatory diseases including rheumatoid arthritis, psoriasis, and multiple sclerosis (Aggarwal et al., *J. Biol. Chem* 278(3): 1910-1914, 2003). Thus, a neutralizing antibody to IL-23 will inhibit the secretion and pro-inflammatory effects of IL-17 and ultimately, the effect of IL-17 on inflammatory diseases.

Although antibodies to human IL-23 have been reported previously, high affinity, neutralizing antibodies to human IL-23 recognizing a specific epitope on the p19 subunit, have not been disclosed. Without question, there is a need for disease modifying therapies for the treatment of autoimmune disease.

Accordingly, there is a need for a high affinity neutralizing antibody that specifically binds the p19 subunit of IL-23 and thereby blocks the pro-inflammatory actions of IL-17, which can be utilized as a therapeutic agent. A high affinity antibody that specifically binds the p19 subunit of IL-23 is also desirable in that it may allow the antibody to be administered to a patient subcutaneously rather than intravenously. There is also a need for an antibody that specifically binds the p19 subunit of L-23 with a low $IC_{50}$ value in an IL-23 inhibition assay in order to generate a therapeutic anti-IL-23 antibody with a minimum effective therapeutic dose. The present invention satisfies these needs and provides related advantages, therefore providing a useful treatment of autoimmune disease.

SUMMARY OF THE INVENTION

An embodiment of this invention is an antibody or antigen binding portion thereof which specifically binds to the p19 subunit of IL-23, neutralizes L-23 activity, has a $K_D$ of less than about 160 pM, and has an $IC_{50}$ of less than about 20 pM.

Another embodiment is an antibody, or antigen-binding portion thereof, that binds the p19 subunit of IL-23 within amino acid residues 129 to 159 of the amino acid sequence shown in SEQ ID NO:60.

Another embodiment of this invention is an antibody or antigen binding portion thereof comprising the heavy chain variable region as shown in SEQ ID NO:52, a light chain variable region as shown in SEQ ID NO:57, a heavy chain constant region as shown in SEQ ID NO:62 and the light chain constant region as shown in SEQ ID NO:63.

Another embodiment of this invention encompasses an antibody or antigen binding portion thereof which specifically binds to the p19 subunit of IL-23 comprising a heavy chain variable region containing an amino acid sequence selected from the group consisting of SEQ ID NOS:44-55 and a light chain variable region containing an amino acid sequence selected from the group consisting of SEQ ID NOS: 56-59.

Another embodiment of the present invention is an antibody or antigen binding portion thereof which specifically binds to the p19 subunit of L-23 comprising a light chain variable region containing an amino acid sequence as shown in SEQ ID NO:57 and a heavy chain variable region containing an amino acid sequence selected from the group consisting of SEQ ID NOs:48, 49, or 52.

In another embodiment, a LCVR of an anti-IL-23 monoclonal antibody of the invention comprises 1, 2 or 3 peptides selected from the group consisting of peptides with a sequence as shown in (a) SEQ ID NOs:26-35; (b) SEQ ID NOs:37-38, and (c) SEQ ID NO:40 (i.e., one peptide from (a), one peptide from (b) and one peptide from (c) for an antibody comprising 3 said peptides), at LCDR1, LCDR2, and LCDR3, respectively.

In another embodiment, a HCVR of an anti-IL-23 monoclonal antibody of the invention comprises 1, 2 or 3 peptides selected from the group consisting of peptides with a sequence as shown in (a) SEQ ID NOs:1-4; (b) SEQ ID NOs:5-11, and (c) SEQ ID NOs:13-21 (i.e., one peptide from (a), one peptide from (b) and one peptide from (c) for an antibody comprising 3 said peptides), at HCDR1, HCDR2, and HCDR3, respectively.

The present invention further provides an anti-IL-23 monoclonal antibody comprising six peptides selected from the group consisting of peptides with a sequence as shown in (a) SEQ ID NOs:26-35; (b) SEQ ID NOs:37-38, (c) SEQ ID NO:40, (d) SEQ ID NOs:1-4; (e) SEQ ID NOs:5-11, and (f) SEQ ID NOs:13-21 (i.e., one peptide from each of (a-f)), at LCDR1, LCDR2, LCDR3, HCDR1, HCDR2, and HCDR3, respectively.

The present invention further provides an anti-IL-23 monoclonal antibody comprising the six peptides with the sequence as shown in SEQ ID NOs:41, 42, 43, at LCDR1, LCDR2, and LCDR3, respectively and SEQ ID NOS:22, 23 and 24, HCDR1, HCDR2, and HCDR3, respectively.

Another embodiment of the invention provides humanized anti-IL-23 monoclonal antibodies, and antigen-binding portions thereof, that bind a specific epitope comprising amino acid residues 129 to 159 of the p19 subunit of IL-23; (residues 129-159 of SEQ ID NO:60), and antagonize or neutralize at least one in vitro or in vivo biological activity associated with IL-23 or a portion thereof.

In another embodiment, antibodies of the invention have an $IC_{50}$ of less than or equal to about 100 pM, 75 pM, 50 pM, 25 pM, 20 pM, 15 pM, 13 pM, 10 pM, 8 pM, 5 pM, 2 pM, or 1 pM in an in vitro murine splenocyte assay as described in Example 1. Preferably, the antibodies of the invention have an $IC_{50}$ of less than or equal to about 20 pM.

In another embodiment, antibodies of the invention are characterized by a strong binding affinity ($K_D$) for the p19 subunit of human IL-23, i.e. less than about 160 pM, 100 pM, 75 pM, 50 pM, or 25 pM. Preferably, the antibodies of the invention have a $K_D$ Of less than about 100 pM. Moreover, the antibodies of the invention are further characterized with a $k_{off}$ rate from the p19 subunit of human IL-23 of less than 4× $10^{-4}$ s$^{-1}$.

Another embodiment of the present invention includes the isolated antibody of any one of the above embodiments wherein the antibody is a full-length antibody, a substantially intact antibody, a chimeric antibody, a Fab fragment, a F(ab')$_2$ fragment or a single chain Fv fragment. Preferably, the isolated antibody, or antigen-binding portion thereof, of any of the above embodiments is a humanized antibody.

The invention includes isolated nucleic acids comprising polynucleotides that encode the antibodies described and claimed herein. The invention also encompasses host cells transfected with vectors containing these polynucleotides that express the antibodies described and claimed herein.

The invention encompasses a method of treating autoimmune disease which comprises administering to a subject an effective amount of an antibody described and claimed herein. Preferably, the autoimmune disease treated is multiple sclerosis.

Finally, the invention encompasses the use of an antibody for the manufacture of a medicament for treating autoimmune disease in a subject in need thereof.

DETAILED DESCRIPTION OF THE INVENTION

This present invention provides amino acid sequences of isolated human antibodies, or antigen-binding portions thereof, that specifically bind the p19 subunit of IL-23 and are useful for the treatment of autoimmune disease.

In order that the present invention may be more readily understood, certain terms are first defined.

The p19 subunit of human IL-23 is a 189 amino acid polypeptide containing a 21 aa leader sequence [SEQ ID NO:60].

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or VH) and a heavy chain constant region (abbreviated herein as HCCR or CH). The heavy chain constant region is comprised of three domains, CH1, CH2 and CH3. Each light chain is comprised of a light chain variable region (abbreviated herein as LCVR or VL) and a light chain constant region (abbreviated herein as LCCR). The light chain constant region is comprised of one domain, CL.

The HCVR and LCVR regions can be further subdivided into regions of hypervariability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein the 3 CDRs of the heavy chain are referred to as "HCDR1, HCDR2, and HCDR3" and the 3 CDRs of the light chain are referred to as "LCDR1, LCDR2 and LCDR3." The CDRs contain most of the residues which form specific interactions with the antigen. The numbering and positioning of CDR amino acid residues within the HCVR and LCVR regions is in accordance with the well-known Kabat numbering convention.

Light chains are classified as kappa and lambda. Heavy chains are classified as gamma, mu, alpha, delta, or epsilon, and define the antibody's isotype as IgG (subclasses IgG$_1$, IgG$_2$, IgG$_3$ and IgG$_4$), IgM, IgA, IgD and IgE, respectively.

Within light and heavy chains, the variable and constant regions are joined by a "J" region of about 12 or more amino acids, with the heavy chain also including a "D" region of about 3 or more amino acids.

The term "antigen-binding portion" of an antibody, as used herein, refers to one or more fragments of an antibody that retain the ability to specifically bind to an antigen (e.g., the p19 subunit of IL-23). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

The CDRs of the antigen-binding region of the antibodies of the invention are entirely or substantially of murine origin, optionally with certain amino acid residues altered, e.g., substituted with a different amino acid residue, (see e.g., Tables 1 and 2) to optimize a particular property of the antibody, e.g., $K_D$, $k_{off}$, $IC_{50}$. In other embodiments, the antigen-binding region of an IL-23 antibody of the invention can be derived from other non-human species including, but not limited to, rabbit, rat or hamster. Alternatively, the antigen-binding region can be derived from human sequence.

The term "monoclonal antibody" as used herein is not limited to antibodies produced through hybridoma technology. "Monoclonal antibody" refers to an antibody that is derived from a single copy or clone, including e.g., eukaryotic, prokaryotic, or phage clone, and not the method by which it is produced. A "monoclonal antibody" can be an intact antibody (comprising a complete or full-length Fc region), a substantially intact antibody, or a portion or fragment of an antibody comprising an antigen-binding portion, e.g., a Fab fragment, Fab' fragment or F(ab')$_2$ fragment of a murine antibody or of a chimeric, humanized or human antibody.

The term "humanized antibody" means an antibody that is composed partially or fully of amino acid sequences derived from a human antibody germline or a rearranged sequence and made by altering the sequence of an antibody having non-human (preferably a mouse monoclonal antibody) complementarity determining regions (CDR). The framework regions of the variable regions are substituted by corresponding human framework regions (or a significant or substantial portion thereof, i.e., at least about 90%, 92%, 94%, 95%, 96%, 97%, 98% or 99%, and follow Kabat numbering)

and are encoded by nucleic acid sequence information that occurs in the human germline immunoglobulin region or in recombined or mutated forms thereof whether or not said antibodies are produced in a human cell.

The CDRs of a humanized antibody may be altered or optimized from the CDRs of a non-human parent antibody from which they originated to generate desired properties, e.g., specificity, affinity and/or preferential binding. Altered or optimized CDRs may have amino acid substitutions, additions and/or deletions when compared to a parent CDRs, preferably about 1, 2, 3, 4, 5, 6, 7, 8, 9 or 10 total within the six CDR domains. For example, the amino acid positions of CDRs that are in SEQ ID NOS: 44-59 are positions which have been altered from the CDRs as shown for Mab3A8. Alternatively murine antibody Mab3A8 may be a parent antibody for comparison of CDRs of an antibody of the invention. As discussed herein, antibody in the context of humanized antibody is not limited to a full-length antibody and can include fragments and single chain forms.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis and thus the amino acid sequences of the VH and VL regions of the recombinant antibodies are sequences that, while derived from and related to human germline VH and VL sequences, may not naturally exist within the human antibody germline repertoire in vivo.

An "isolated antibody", as used herein, is intended to refer to an antibody that is substantially free of other antibodies having different antigenic specificities (e.g., an isolated antibody that specifically binds the p19 subunit of human IL-23 is substantially free of antibodies that specifically bind other antigens). An isolated antibody that specifically binds the p19 subunit of human IL-23 may, however, have cross-reactivity to other antigens, such as IL-23 molecules from other species. Moreover, an isolated antibody may be substantially free of other cellular material and/or chemicals.

A "neutralizing antibody", as used herein, is intended to refer to an antibody whose binding to the p19 subunit of human IL-23 results in inhibition of the biological activity of human IL-23. Measuring one or more indicators of IL-23 biological activity as determined using either the mouse splenocyte bioassay [Example 1] or the human IL-23 neutralization assay [Example 2] can assess this inhibition of the biological activity of human IL-23.

A "variant" antibody, refers herein to a molecule which differs in amino acid sequence from a "parent" antibody amino acid sequence by virtue of addition, deletion and/or substitution of one or more amino acid residue(s) of the parent antibody sequence. In a preferred embodiment, the variant antibody comprises at least one amino acid addition, deletion and/or substitution in the CDR regions of the parent antibody (e.g., from one to about ten, and preferably 2, 3, 4, 5, 6, 7 or 8). Identity or homology with respect to the variant antibody sequence is defined herein as the percentage of amino acid residues in the variant antibody sequence that are identical with the parent antibody residues after aligning the sequences and introducing gaps, if necessary, to achieve the maximum percent sequence identity. The variant antibody retains the ability to bind the antigen, or preferably, the epitope, to which the parent antibody binds and preferably has at least one property or bioactivity that is superior to that of the parent antibody. For example, the variant antibody preferably has stronger binding affinity, slower off-rate, lower $IC_{50}$ or enhanced ability to inhibit an antigen bioactivity than does the parent antibody. A variant antibody of particular interest herein is one which displays at least about 2-fold, preferably at least about 5-fold, 10-fold or 20-fold enhancement in a property or bioactivity when compared to the parent antibody.

The "parent" antibody herein is one which contains the amino acid sequence used for the preparation of a variant antibody. The parent antibody may have framework sequence of murine origin, but preferably the framework sequence is entirely or substantially of human origin. The parent antibody may be a murine, chimeric, humanized or human antibody.

Antibodies that "specifically bind" bind the p19 subunit of human IL-23 but do not bind the p40 subunit of human IL-23. An antibody that specifically binds human IL-23 may show some cross-reactivity with IL-23 from other species.

The term "epitope" refers to that portion of a molecule capable of being recognized by and bound by an antibody at one or more of the antibody's antigen-binding regions. Epitopes often consist of a chemically active surface grouping of molecules such as amino acids or sugar side chains and have specific three-dimensional structural characteristics as well as specific charge characteristics. By "inhibiting epitope" and/or "neutralizing epitope" is intended an epitope, which when in the context of the intact antigenic molecule and when bound by an antibody specific to the epitope, results in loss or diminution of a biological activity of the molecule in vivo or in vitro or in an organism containing the molecule. The term "antigenic epitope," as used herein, is defined as a portion of a polypeptide to which an antibody can specifically bind as determined by any method well known in the art, for example, by conventional immunoassays. A "nonlinear epitope" or "conformational epitope" comprises noncontiguous polypeptides (or amino acids) within the antigenic protein to which an antibody specific to the epitope binds.

The term "$k_{on}$", as used herein is intended to refer to the association or on rate constant, or specific reaction rate, of the forward, or complex-forming, reaction, measured in units: $M^{-1}sec^{-1}$.

The term "$k_{off}$", as used herein, is intended to refer to the dissociation or off rate constant, or specific reaction rate, for dissociation of an antibody from the antibody/antigen complex, measured in units: $sec^-$.

The term "$K_D$", as used herein, is intended to refer to the dissociation constant of a particular antibody-antigen interaction. It is calculated by the formula:

$$k_{off}/k_{on}=K_D$$

The antibodies of the present invention are high affinity antibodies, generally exhibiting low $k_{off}$ values. For purposes of the present disclosure, the term "high affinity" refers to an affinity or $K_D$ of between $1.6\times10^{-10}$ M to about $4.5\times10^{-11}$ M.

The term "potency" is a measurement of biological activity and is designated as $IC_{50}$, or effective concentration of antibody needed to neutralize 50% of the bioactivity of IL-23 on mouse splenocytes in the bioassay described in Example 1.

The term "nucleic acid molecule", as used herein, is intended to include DNA molecules and RNA molecules. A nucleic acid molecule may be single-stranded or double-stranded, but preferably is double-stranded DNA.

The term "isolated nucleic acid molecule", as used herein in reference to nucleic acids encoding antibodies or antibody portions (e.g., VH, VL, CDR3) that bind human IL-23, is intended to refer to a nucleic acid molecule in which the nucleotide sequences encoding the antibody or antibody portion are free of other nucleotide sequences encoding antibodies or antibody portions that bind antigens other than human IL-23, which other sequences may naturally flank the nucleic acid in human genomic DNA. Thus, for example, an isolated nucleic acid of the invention encoding a VH region of an anti-human IL-23 antibody contains no other sequences encoding other VH regions that bind antigens other than human IL-23.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome.

The term "recombinant host cell" (or simply "host cell"), as used herein, is intended to refer to a cell into which a recombinant expression vector has been introduced.

Monoclonal antibody 3A8 is a murine monoclonal antibody (MAb3A8) that specifically binds to an epitope on the p19 subunit of human IL-23. MAb3A8 was humanized and optimized resulting in high affinity antibodies with potent IL-23 neutralizing activity and highly specific for the p19 subunit but not the p40 subunit of IL-23.

The preferred antibodies or antigen-binding portions thereof of the present invention exhibit high affinity (low $K_D$ values) for the same epitope as MAb3A8 and have binding affinity superior to that observed for MAb3A8. The binding properties that define the antibodies of the present invention reside solely in the variable regions of the antibody, more specifically the CDR regions of the antibody.

The primary impetus for humanizing antibodies from another species is to reduce the possibility that the antibody causes an immune response when injected into a human patient as a therapeutic. The more human sequences that are employed in a humanized antibody, the lower the risk of immunogenicity. In addition, the injected humanized antibodies generally have a longer half-life in the circulation than injected non-human antibodies. Furthermore, if effector function is desired, because the effector portion is human, it may interact better with the other parts of the human immune system. Changes can be made to the sequences described herein as preferable heavy and light chain regions without significantly affecting the biological properties of the antibody. This is especially true for the antibody constant regions and parts of the variable regions that do not influence the ability of the CDRs to bind to IL-23.

Furthermore, as discussed herein, human framework variable regions and variants thereof may be used in the present invention. However, regardless of the framework chosen, if reducing the risk of immunogenicity is a focus, the number of changes relative to the human framework chosen are minimized.

The humanized antibody of the present invention may comprise or be derived from a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the humanized antibody of the present invention may comprise or be derived from a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework. In other embodiments, at least FRH1, FRH2, FRH3, or FRH4 is a germline sequence (e.g., human germline) or comprises human consensus sequences for the particular framework. In preferred embodiments, all of the framework region is human framework region.

Preferred human heavy chain constant region amino acid sequences of the humanized antibodies of the present invention include the IgG1 constant region IgG1 [SEQ ID NO:61] or the IgG4 constant region [SEQ ID NO:62]. The preferred human light chain constant region amino acid sequence of the humanized antibodies of the present invention is the kappa chain constant region [SEQ ID NO:63].

Furthermore, the preferred human variable heavy chain region frame work is VH1-24 [SEQ ID NO:64] and the preferred human variable light chain region framework is A17 [SEQ ID NO:65]. SEQ ID NOS: 64 and 65 represent the human germline sequences with native CDRs. The CDRs from MAb3A8 are added along with the best match human J regions to form the complete variable regions. It is understood that additional human heavy or light chain constant regions and variable region framework sequences other than those described above are contemplated for the present invention and are known in the art.

The present invention encompasses antibodies or antigen-binding portions thereof that bind to a specific epitope on the p19 subunit of IL-23 and neutralize the activity of IL-23. Thus, the CDRs and heavy and light chain variable regions described herein are used to make full-length antibodies as well as functional fragments and analogs that maintain the binding affinity of the protein employing the CDRs specific for p19 subunit of IL-23.

The binding affinity of MAb3A8 is determined using surface plasmon resonance (BLAcore™). In these experiments the antibody is captured at low density by either protein A or anti-Fc antibody on a BIAcore™ chip and ligand is flowed past. Build up of mass at the surface of the chip is measured. This analytical method allows the determination in real time of both on and off rates to obtain affinity ($K_D$) for binding. MAb3A8 has a $K_D$ of approximately 300 pM (picomolar). The humanized antibodies of the present invention, have a $K_D$ of between about 45 and about 160 pM; about 45 and about 150 pM; about 45 and about 100 pM; about 50 and about 95 pM; about 60 and about 85 pM; and, about 70 and about 80 pM. Preferably, the humanized antibodies of the present invention, have a $K_D$ of less than about 100 pM.

The antibodies or antigen-binding portions thereof of the present invention neutralize the biological activity of IL-23. Two assays are utilized to test the ability of MAb3A8 and preferred antibodies of the present invention to neutralize IL-23 activity [see Examples 1 and 2].

The present invention also is directed to recombinant DNA encoding antibodies which, when expressed, specifically bind to the p19 subunit of human IL-23. Preferably, the DNA encodes antibodies that, when expressed, comprise one or more of the heavy and light chain CDRs of the present invention [Tables 1 and 2].

TABLE 1

CDR Sequences-Heavy Chain Variable Region (HCDR)

| FAb | HCDR1 | HCDR2 | HCDR3 |
|---|---|---|---|
| 3A8 | GKTFTSYGIN (SEQ ID NO: 1) | YIYIGNGYTESNEKFKG (SEQ ID NO: 5) | IGAYYGNFDY (SEQ ID NO: 12) |
| 1 | GKTFFSYGIN (SEQ ID NO: 2) | YIYIGGGYTEPNPKYKG (SEQ ID NO: 6) | IGGYYGNETD (SEQ ID NO: 13) |
| 2 | GKTFWSYGIN (SEQ ID NO. 3) | YIYIGGGYTEPNPKYKG (SEQ ID NO. 6) | IGGYYGNFTD (SEQ ID NO: 13) |
| 3 | GKTFFSYGIN (SEQ ID NO: 2) | YIYIGNGYTEPNPKYKG (SEQ ID NO: 7) | IGGYYGNFTD (SEQ ID NO: 13) |
| 4 | GKTFWSYGIN (SEQ ID NO: 3) | YIYIGGGYTEPNPKYKG (SEQ ID NO. 6) | IGGYYGNFTD (SEQ ID NO: 13) |
| 5 | GKTFFSYGIN (SEQ ID NO: 2) | YIYIGNGYTEPNPKYKG (SEQ ID NO: 7) | IGGYYGNFTD (SEQ ID NO: 13) |
| 6 | GKTFYSYGIN (SEQ ID NO. 4) | YIYIGNGYTEPNPKYKG (SEQ ID NO: 7) | IGGYYGNFTD (SEQ ID NO: 13) |
| 7 | GKTFWSYGIN (SEQ ID NO: 3) | YIYIGGGYTEPNPKYKG (SEQ ID NO: 6) | IGGYYGNFTD (SEQ ID NO: 13) |
| 8 | GKTFWSYGIN (SEQ ID NO: 3) | YIYIGNGYTEPNPKYKG (SEQ ID NO: 7) | IGGYYGNFTD (SEQ ID NO: 13) |
| 9 | GKTFWSYGIN (SEQ ID NO: 3) | YIYIGNGYTEPNPKYKG (SEQ ID NO: 7) | IGGYYGNFTD (SEQ ID NO: 13) |
| 10 | GKTFWSYGIN (SEQ ID NO: 3) | YIYIGGGYTEPNPKYKG (SEQ ID NO: 6) | IGGYYGNFTD (SEQ ID NO: 13) |
| 11 | GKTFWSYGIN (SEQ ID NO: 3) | YIYIGNGYTEPNPKYKG (SEQ ID NO: 7) | IGGYYGNFTD (SEQ ID NO: 13) |
| 12 | GKTFWSYGIN (SEQ ID NO: 3) | YIYIGNGYTEPNPKYKG (SEQ ID NO: 7) | IGGYYGNFTD (SEQ ID NO: 13) |
| 13 | GKTFWSYGIN (SEQ ID NO: 3) | YIYIGGGYTEPNPKYKG (SEQ ID NO: 6) | IGGYYGNFDD (SEQ ID NO. 14) |
| 14 | GKTFWSYGIN (SEQ ID NO: 3) | YIYIGNGYTEPNPKYKG (SEQ ID NO: 7) | IGGYYGNFTD (SEQ ID NO: 13) |
| 15 | GKTFWSYGIN (SEQ ID NO: 3) | YIYIGGGYTEPNPKYKG (SEQ ID NO: 6) | IGGYYGNFTD (SEQ ID NO: 13) |
| 16 | GKTFTSYGIN (SEQ ID NO: 1) | YIYIGGGYTEPNPKYKG (SEQ ID NO: 6) | IGGYYGNFTD (SEQ ID NO: 13) |
| 17 | GKTFWSYGIN (SEQ ID NO: 3) | YIYIGGGYTEPNPKYKG (SEQ ID NO: 6) | IGGYYGNFTD (SEQ ID NO: 13) |
| 18 | GKTFFSYGIN (SEQ ID NO: 2) | YIYIGNGYTEPNPKYKG (SEQ ID NO: 7) | IGGYYGNFDD (SEQ ID NO. 14) |
| 19 | GKTFWSYGIN (SEQ ID NO: 3) | YIYIGGGYTEPNPKYKG (SEQ ID NO: 6) | IGGYYGNFTD (SEQ ID NO: 13) |
| 20 | GKTFWSYGIN (SEQ ID NO: 3) | YIYIGNGYTEPNPKYKG (SEQ ID NO: 7) | IGGYYGNFDD (SEQ ID NO. 14) |
| 21 | GKTFFSYGIN (SEQ ID NO: 2) | YIYIGNGYTEPNPKYKG (SEQ ID NO: 7) | IGGYYGNFTD (SEQ ID NO: 13) |

TABLE 1-continued

CDR Sequences-Heavy Chain Variable Region (HCDR)

| FAb | HCDR1 | HCDR2 | HCDR3 |
|---|---|---|---|
| 22 | GKTFWSYGIN (SEQ ID NO: 3) | YIYIGNGYTEPNPKYKG (SEQ ID NO: 7) | IGGYYGNFDD (SEQ ID NO. 14) |
| 23 | GKTFFSYGIN (SEQ ID NO: 2) | YIYIGNGYTEPNPKYKG (SEQ ID NO: 7) | IGGYYGNFTD (SEQ ID NO: 13) |
| 24 | GKTFWSYGIN (SEQ ID NO: 3) | YIYIGNGYTEPNPKYKG (SEQ ID NO: 7) | IGGYYGNFTD (SEQ ID NO: 13) |
| 25 | GKTFWSYGIN (SEQ ID NO: 3) | YIYIGNGYTEPNPKYKG (SEQ ID NO: 7) | IGGYYGNETD (SEQ ID NO: 13) |
| 26 | GKTFWSYGIN (SEQ ID NO: 3) | YIYIGGGYTEPNPKYKG (SEQ ID NO: 6) | IGGYYGNFTD (SEQ ID NO: 13) |
| 27 | GKTFWSYGIN (SEQ ID NO: 3) | YIYIGNGYTEPNPKYKG (SEQ ID NO: 7) | IGGYYGNFDD (SEQ ID NO. 14) |
| 28 | GKTFWSYGIN (SEQ ID NO: 3) | YIYIGNGYTEPNPKYKG (SEQ ID NO: 7) | IGGYYGNFTD (SEQ ID NO: 13) |
| 29 | GKTFWSYGIN (SEQ ID NO: 3) | YIYIGGGYTEPNPKYKG (SEQ ID NO: 6) | IGGYYGNFDD (SEQ ID NO. 14) |
| 30 | GKTFWSYGIN (SEQ ID NO: 3) | YIYIGNGYTEPNPKYKG (SEQ ID NO: 7) | IGGYYGNFHD (SEQ ID NO. 15) |
| 31 | GKTFWSYGIN (SEQ ID NO: 3) | YIYIGTGYTEPNPKYKG (SEQ ID NO: 8) | IGGYYGNFAD (SEQ ID NO: 16) |
| 32 | GKTFWSYGIN (SEQ ID NO: 3) | YIYIGSGYTEPNPKYKG (SEQ ID NO: 9) | IGGYYGNFHD (SEQ ID NO: 15) |
| 33 | GKTFWSYGIN (SEQ ID NO: 3) | YIYIGTGYTEPNPKYKG (SEQ ID NO: 8) | IGGYYGNFKD (SEQ ID NO: 17) |
| 34 | GKTFWSYGIN (SEQ ID NO: 3) | YIYIGTGYTEPNPKYKG (SEQ ID NO: 8) | IGGYYGNFDH (SEQ ID NO: 18) |
| 35 | GKTFWSYGIN (SEQ ID NO: 3) | YIYIGTGYTEPNPKYKG (SEQ ID NO: 8) | IGGYYGNFDQ (SEQ ID NO: 19) |
| 36 | GKTFWSYGIN (SEQ ID NO: 3) | YIYIGRGYTEPNPKYKG (SEQ ID NO: 10) | IGGYYGNFQD (SEQ ID NO: 20) |
| 37 | GKTFWSYGIN (SEQ ID NO: 3) | YIYIGYGYTEPNPKYKG (SEQ ID NO: 11) | IGGYYGNFED (SEQ ID NO: 21) |
| 38 | GKTFWSYGIN (SEQ ID NO: 3) | YIYIGTGYTEPNPKYKG (SEQ ID NO: 8) | IGGYYGNFED (SEQ ID NO: 21) |
| Consensus Sequence* | GKTFX$_1$SYGIN (SEQ ID NO: 22) | YIYIGX$_2$GYTEX$_3$NX$_4$KX$_5$KG (SEQ ID NO: 23) | IGX$_6$YYGNFX$_7$X$_8$ (SEQ ID NO: 24) |

*X$_1$ is T, F, W, or Y; X$_2$ is N, T, S, R, Y, or G; X$_3$ is S or P; X$_4$ is E or P; X$_5$ is F or Y; X$_6$ is A or G; X$_7$ is D, H, A, K, Q, E, or T; and X$_8$ is Y, H, Q or D.

TABLE 2

CDR Sequences-Light Chain Variable Region (LCVR)

| FAb | LCDR1 | LCDR2 | LCDR3 |
|---|---|---|---|
| MAb3A8 | KSSQSLLDSDGKTYLN (SEQ ID NO: 25) | LVSKLDS (SEQ ID NO: 36) | WQGTHFPLT (SEQ ID NO: 39) |
| 1 | QSSQSLLISGGNTYLN (SEQ ID NO: 26) | LVSKLDQ (SEQ ID NO: 37) | WQGTYFPLT (SEQ ID NO: 40) |
| 2 | QSSQSLLISGGKTYLN (SEQ ID NO: 27) | LVSKLDQ (SEQ ID NO: 37) | WQGTYFPLT (SEQ ID NO: 40) |

TABLE 2-continued

CDR Sequences-Light Chain Variable Region (LCVR)

| FAb | LCDR1 | LCDR2 | LCDR3 |
|---|---|---|---|
| 3 | QSSQSLLISGGNTYLN (SEQ ID NO: 26) | LVSKLDQ (SEQ ID NO: 37) | WQGTYFPLT (SEQ ID NO: 40) |
| 4 | QSSQSLLISGGNTYLN (SEQ ID NO: 26) | LVSKLDQ (SEQ ID NO: 37) | WQGTYFPLT (SEQ ID NO: 40) |
| 5 | RSSQSLLISGGNTYLN (SEQ ID NO: 28) | LVSKLDQ (SEQ ID NO: 37) | WQGTYFPLT (SEQ ID NO: 40) |
| 6 | QSSQSLLISGGNTYLN (SEQ ID NO: 26) | LVSKLDQ (SEQ ID NO: 37) | WQGTYFPLT (SEQ ID NO: 40) |
| 7 | QSSQSLLISGGKTYLN (SEQ ID NO: 27) | LVSKLDQ (SEQ ID NO: 37) | WQGTYFPLT (SEQ ID NO: 40) |
| 8 | QSSQSLLISGGNTYLN (SEQ ID NO: 26) | LVSKLDQ (SEQ ID NO: 37) | WQGTYFPLT (SEQ ID NO: 40 |
| 9 | RSSQSLLISGGNTYLN (SEQ ID NO: 28) | LVSKLDQ (SEQ ID NO: 37) | WQGTYFPLT (SEQ ID NO: 40) |
| 10 | RSSQSLLISGGNTYLN (SEQ ID NO: 28) | LVSKLDQ (SEQ ID NO: 37) | WQGTYFPLT (SEQ ID NO: 40) |
| 11 | RSSQSLLISGGKTYLN (SEQ ID NO: 29) | LVSKLDQ (SEQ ID NO: 37) | WQGTYFPLT (SEQ ID NO: 40) |
| 12 | KSSQSLLISGGNTYLN (SEQ ID NO: 30) | LVSKLDQ (SEQ ID NO: 37) | WQGTYFPLT (SEQ ID NO: 40) |
| 13 | KSSQSLLISGGKTYLN (SEQ ID NO: 31) | KVSKLDQ (SEQ ID NO: 38) | WQGTYFPLT (SEQ ID NO: 40) |
| 14 | QSSQSLLISGGKTYLN (SEQ ID NO: 27) | LVSKLDQ (SEQ ID NO: 37) | WQGTYFPLT (SEQ ID NO: 40) |
| 15 | KSSQSLLISGGKTYLN (SEQ ID NO: 31) | LVSKLDQ (SEQ ID NO: 37) | WQGTYFPLT (SEQ ID NO: 40) |
| 16 | RSSQSLLISGGPTYLN (SEQ ID NO: 32) | LVSKLDQ (SEQ ID NO: 37) | WQGTYFPLT (SEQ ID NO: 40) |
| 17 | RSSQSLLISGGPTYLN (SEQ ID NO: 32) | KVSKLDQ (SEQ ID NO: 37) | WQGTYFPLT (SEQ ID NO: 40) |
| 18 | KSSQSLLISGGKTYLN (SEQ ID NO: 31) | KVSKLDQ (SEQ ID NO: 38) | WQGTYFPLT (SEQ ID NO: 40) |
| 19 | KSSQSLLISGGKTYLN (SEQ ID NO: 31) | KVSKLDQ (SEQ ID NO: 38) | WQGTYFPLT (SEQ ID NO: 40) |
| 20 | KSSQSLLISGGKTYLN (SEQ ID NO: 31) | LVSKLDQ (SEQ ID NO: 37) | WQGTYFPLT (SEQ ID NO: 40) |
| 21 | KSSQSLLISGGKTYLN (SEQ ID NO: 31) | LVSKLDQ (SEQ ID NO: 37) | WQGTYFPLT (SEQ ID NO: 40) |
| 22 | KSSQSLLISGGKTYLN (SEQ ID NO: 31) | KVSKLDQ (SEQ ID NO: 38) | WQGTYFPLT (SEQ ID NO: 40) |
| 23 | QSSQSLLISGGKTYLN (SEQ ID NO: 27) | KVSKLDQ (SEQ ID NO: 38) | WQGTYFPLT (SEQ ID NO: 40) |
| 24 | KSSQSLLISGGKTYLN (SEQ ID NO: 31) | KVSKLDQ (SEQ ID NO: 38) | WQGTYFPLT (SEQ ID NO: 40) |
| 25 | QSSQSLLISGGPTYLN (SEQ ID NO: 33) | KVSKLDQ (SEQ ID NO: 38) | WQGTYFPLT (SEQ ID NO: 40) |
| 26 | KSSQSLLISGGPTYLN (SEQ ID NO: 34) | KVSKLDQ (SEQ ID NO: 38) | WQGTYFPLT (SEQ ID NO: 40) |
| 27 | KSSQSLLISGGNTYLN (SEQ ID NO: 35) | KVSKLDQ (SEQ ID NO: 38) | WQGTYFPLT (SEQ ID NO: 40) |

TABLE 2-continued

CDR Sequences-Light Chain Variable Region (LCVR)

| FAb | LCDR1 | LCDR2 | LCDR3 |
|---|---|---|---|
| 28 | RSSQSLLISGGNTYLN (SEQ ID NO: 28) | LVSKLDQ (SEQ ID NO: 37) | WQGTYFPLT (SEQ ID NO: 40) |
| 29 | KSSQSLLISGGKTYLN (SEQ ID NO: 31) | LVSKLDQ (SEQ ID NO: 37) | WQGTYFPLT (SEQ ID NO: 40) |
| 30 | RSSQSLLISGGNTYLN (SEQ ID NO: 28) | LVSKLDQ (SEQ ID NO: 37) | WQGTYFPLT (SEQ ID NO: 40) |
| 31 | RSSQSLLISGGNTYLN (SEQ ID NO: 28) | LVSKLDQ (SEQ ID NO: 37) | WQGTYFPLT (SEQ ID NO: 40) |
| 32 | RSSQSLLISGGNTYLN (SEQ ID NO: 28) | LVSKLDQ (SEQ ID NO: 37) | WQGTYFPLT (SEQ ID NO: 40) |
| 33 | RSSQSLLISGGNTYLN (SEQ ID NO: 28) | LVSKLDQ (SEQ ID NO: 37) | WQGTYFPLT (SEQ ID NO: 40) |
| 34 | RSSQSLLISGGNTYLN (SEQ ID NO: 28) | LVSKLDQ (SEQ ID NO: 37) | WQGTYFPLT (SEQ ID NO: 40) |
| 35 | RSSQSLLISGGNTYLN (SEQ ID NO: 28) | LVSKLDQ (SEQ ID NO: 37) | WQGTYFPLT (SEQ ID NO: 40) |
| 36 | RSSQSLLISGGNTYLN (SEQ ID NO: 28) | LVSKLDQ (SEQ ID NO: 37) | WQGTYFPLT (SEQ ID NO: 40) |
| 37 | RSSQSLLISGGNTYLN (SEQ ID NO: 28) | LVSKLDQ (SEQ ID NO: 37) | WQGTYFPLT (SEQ ID NO: 40) |
| 38 | RSSQSLLISGGNTYLN (SEQ ID NO: 28) | LVSKLDQ (SEQ ID NO: 37) | WQGTYFPLT (SEQ ID NO: 40) |
| Consensus Sequence** | $X_9$SSQSLL$X_{10}$S$X_{11}$G$X_{12}$TYLN (SEQ ID NO: 41) | $X_{13}$VSKLD$X_{14}$ (SEQ ID NO: 42) | WQGT$X_{15}$FPLT (SEQ ID NO: 43) |

**$X_9$ is K, Q, or R; $X_{10}$ is D or I; $X_{11}$ is D or G; $X_{12}$ is K, N, or P; $X_{13}$ is L or K; $X_{14}$ is S or Q; and $X_{15}$ is H or Y.

The invention includes antibodies comprising the consensus sequences for the light chain CDRs as represented by SEQ ID NOS: 41, 42, and 43 and for the heavy chain CDRs as represented by SEQ ID NOS: 22, 23 and 24. Exemplary amino acid sequences of the heavy chain variable regions of the preferred antibodies of the present invention utilizing the VH framework VH1-24 are represented as SEQ ID NOS: 44-55. Exemplary amino acid sequences of the light chain variable regions of the preferred antibodies of the present invention utilizing the VL framework A17 are represented as SEQ ID NOS: 56-59. Amino acid residue 41 of SEQ ID NOS: 58 and 59 is changed to the murine residue located at this position. Moreover, exemplary antibodies of the present invention are represented by a heavy chain constant region as shown in SEQ ID NO:62 and, a light chain constant region as shown in SEQ ID NO: 63.

Thus, exemplary antibodies of the invention are selected from the group consisting of:

(a) an antibody with a LCVR as shown in SEQ ID NO:57, a HCVR as shown in SEQ ID NO: 47, a LCCR as shown in SEQ ID NO:63, and a HCCR as shown in SEQ ID NO:62;

(b) an antibody with a LCVR as shown in SEQ ID NO:57, a HCVR as shown in SEQ ID NO: 48, a LCCR as shown in SEQ ID NO:63, and a HCCR as shown in SEQ ID NO:62;

(c) an antibody with a LCVR as shown in SEQ ID NO:57, a HCVR as shown in SEQ ID NO: 49, a LCCR as shown in SEQ ID NO:63, and a HCCR as shown in SEQ ID NO:62;

(d) an antibody with a LCVR as shown in SEQ ID NO:57, a HCVR as shown in SEQ ID NO: 51, a LCCR as shown in SEQ ID NO:63, and a HCCR as shown in SEQ ID NO:62;

(e) an antibody with a LCVR as shown in SEQ ID NO:57, a HCVR as shown in SEQ ID NO: 52, a LCCR as shown in SEQ ID NO:63, and a HCCR as shown in SEQ ID NO:62;

(f) an antibody with a LCVR as shown in SEQ ID NO:57, a HCVR as shown in SEQ ID NO: 53, a LCCR as shown in SEQ ID NO:63, and a HCCR as shown in SEQ ID NO:62; and, (g) an antibody with a LCVR as shown in SEQ ID NO:57, and, a HCVR as shown in SEQ ID NO: 55, a LCCR as shown in SEQ ID NO:63, and a HCCR as shown in SEQ ID NO:62.

The neutralizing antibodies of the present invention are achieved through generating appropriate antibody gene sequences, i.e., amino acid sequences, by arranging the appropriate nucleotide sequences and expressing these in a suitable cell line. Desired nucleotide sequences can be produced using, a method of codon based mutagenesis. Such procedures permit the production of any and all frequencies of amino acid residues at any desired codon positions within an oligonucleotide. This can include completely random substitutions of any of the 20 amino acids at a desired position. Alternatively, this process can be carried out so as to achieve a particular amino acid at a desired location within an amino acid chain, such as the novel CDR sequences according to the invention. In sum, the appropriate nucleotide sequence to express any amino acid sequence desired can be readily achieved and using such procedures the novel CDR sequences of the present invention can be reproduced. This results in the ability to synthesize polypeptides, such as antibodies, with any desired amino acid sequences. For example, it is now possible to determine the amino acid sequence of any desired domain of an antibody of choice and, optionally, to prepare homologous chains with one or more amino acids replaced by other desired amino acids, so as to give a range of substituted analogs.

In applying such methods, it is to be appreciated that due to the degeneracy of the genetic code, such methods as random oligonucleotide synthesis and partial degenerate oligonucleotide synthesis will incorporate redundancies for codons specifying a particular amino acid residue at a particular position, although such methods can be used to provide a master set of all possible amino acid sequences and screen these for optimal function as antibody structures or for other purposes. Alternatively, such antibody sequences can be synthesized chemically or generated in other ways well known to those skilled in the art.

In accordance with the invention disclosed herein, enhanced high potency antibodies can be generated by combining in a single polypeptide structure one or more novel CDR sequences as disclosed herein, each shown to independently result in enhanced potency or biological activity. In this manner, several novel amino acid sequences can be combined into one antibody, in the same or different CDRs, to produce antibodies with desirable levels of biological activity. The amino acid changes have the effect of producing a decrease in the $k_{off}$ for said antibody, preferably with an increase in antibody affinity. Higher potency can be achieved with a lower $k_{off}$ value even if the affinity remains the same or is reduced somewhat. Such an antibody is most advantageously produced by synthesis of the required polypeptide chains via synthesis in suitably engineered cells having incorporated therein the appropriate nucleotide sequences coding for the required polypeptide chains containing the altered CDR segments. By way of a non-limiting example, such novel CDR sequences may be employed and the resulting antibodies screened for potency, or biological activity, using either the splenocyte bioassay or the human IL-23 neutralization protocol described herein, where the antibody demonstrates high affinity for a particular antigenic structure, such as the p19 subunit of human IL-23.

Conversely, it must be appreciated that not all locations within the sequences of the different antibody domains may be equal in that substitutions of any kind in a particular location may be helpful or detrimental. In addition, substitutions of certain kinds of amino acids at certain locations may likewise be a plus or a minus regarding affinity. For example, it may not be necessary to try all possible hydrophobic amino acids at a given position. It may be that any hydrophobic amino acid will do as well. On the other hand, an acidic or basic amino acid at a given location may provide large swings in measured affinity.

As already described, $K_D$ is measured by the ratio of the $k_{on}$ and $k_{off}$ constants. For example, a $k_{on}$ of $3.1 \times 10^7$ $(M^{-1}s^{-1})$ and a $k_{off}$ of $0.9 \times 10^{-4}$ $(s^{-1})$ would combine to give a $K_D$ of $2.9 \times 10^{-12}$M. Thus, affinity can be improved by increasing the $k_{on}$ or decreasing the $k_{off}$. Correspondingly, a decrease in the $k_{off}$ of antibodies of the present invention will likely result in a more efficacious therapeutic agent.

In accordance with the foregoing, the antibodies of the present invention are high affinity monoclonal antibodies. Such antibodies, however, are monoclonal only in the sense that they may be derived from a clone of a single cell type. However, this is not meant to limit them to a particular origin. Such antibodies may readily be produced in cells that commonly do not produce antibodies, such as CHO, NS0, or COS cells. In addition, such antibodies may be produced in other types of cells, especially mammalian and even bacterial and plant cells, by genetically engineering such cells to express and assemble the polypeptide light and heavy chains forming the antibody product. In addition, such chains can be chemically synthesized but, since they would be specific for a given antigenic determinant, would still constitute "monoclonal" antibodies within the spirit in which that term is used. Thus, as used herein, the term monoclonal antibody is intended to denote more the specificity and purity of the antibody molecules rather than the mere mechanism used for production of said antibodies.

Also as used herein, the term potency is intended to describe the dependency of the effect of the antibody, when utilized for its intended therapeutic purpose, on the concentration of such antibody. Thus, potency means biological activity with respect to a given antigen. By way of non-limiting example, the potency, or biological activity, or biological effect, is measured for an anti-IL-23 antibody, by either the splenocyte bioassay or the human IL-23 neutralization protocol described herein. The relative potency of the antibodies produced according to the methods of the present invention, designated as $IC_{50}$, will typically be in the range of about 1 pM to about 100 pM, about 1 pM to about 50 pM; about 1 pM to about 25 pM. Preferably, the $IC_{50}$, will be about 25 pM, 20 pM, 15 pM, 13 pM, 10 pM, 8 pM, 5 pM, 2 pM, or 1 pM. Most preferably, the antibodies of the invention have an $IC_{50}$ of about 20 pM.

Conversely, the affinity of an antibody for the antigen is simply a mathematical measure of the ratio of $k_{on}$ to $k_{off}$. In addition, the $K_D$ of the antibodies produced according to the methods of the present invention will typically be in the range of about $2 \times 10^{-10}$ M to about $25 \times 10^{-12}$M, preferably less than about 160 pM, 100 pM, 75 pM, 50 pM, or 25 pM. Most preferably, the antibodies of the invention have a $K_D$ of less than about 100 pM.

In one embodiment, the antibodies or antigen-binding portions thereof of the present invention will commonly comprise a mammalian, preferably a human, constant region and a variable region, said variable region comprising heavy and light chain framework regions and heavy and light chain CDRs, wherein the heavy and light chain framework regions have sequences characteristic of a mammalian antibody, preferably a human antibody, and wherein the CDR sequences are similar to those of an antibody of some species other than a human, preferably a mouse.

In an embodiment of the present invention, potency is increased using a neutralizing antibody Fab fragment against human IL-23 having a $K_D$ of less than about 160 pM and by decreasing the $k_{off}$ value to less than about $1 \times 10^{-3}$ $s^{-1}$, preferably less than about $5 \times 10^{-4}$ $s^{-1}$, more preferably less than about $1 \times 10^{-4}$ $s^{-1}$. The amino acids present in the CDRs of such Fab fragments are shown in Tables 1 and 2.

In specific embodiments, the present invention relates to an isolated antibody comprising a $K_D$ of less than about 160 pM wherein the $k_{off}$ is less than about $1 \times 10^{-3}$ $s^{-1}$, preferably less than about $5 \times 10^{-4}$ $s^{-1}$, and most preferably less than about $1 \times 10^{-4}$ $s^{-1}$ (including all combinations thereof). Thus, preferred antibodies of the present invention bind to the p19 subunit of mature human IL-23 with a $K_D$ of about 160 pM or less, have a $k_{off}$ rate constant of $1 \times 10^{-3}$ $s^{-1}$ or less, and neutralize human IL-23 activity.

DNA encoding the antibodies of the present invention will typically include an expression control polynucleotide sequence operably linked to the antibody coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, for the collection and purification of the light chains, heavy chains, light/heavy chain dimers or intact antibodies, binding fragments or other immunoglobulin forms.

The nucleic acid sequences of the present invention capable of ultimately expressing the desired antibodies can be formed from a variety of different polynucleotides (genomic or cDNA, RNA, synthetic oligonucleotides, etc.) and components (e.g., V, J, D, and C regions), using any of a variety of well known techniques. Joining appropriate genomic and synthetic sequences is a common method of production, but cDNA sequences may also be utilized.

Human constant region DNA sequences can be isolated in accordance with well known procedures from a variety of human cells, but preferably from immortalized B-cells. Suitable source cells for the polynucleotide sequences and host cells for immunoglobulin expression and secretion can be obtained from a number of sources well-known in the art.

As described herein, in addition to the antibodies specifically described herein, other "substantially homologous" modified antibodies can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in vectors using site-directed mutagenesis, such as after CH1 to produce Fab fragments or after the hinge region to produce F(ab')$_2$ fragments. Single chain antibodies may be produced by joining VL and VH with a DNA linker.

As stated previously, the polynucleotides will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

*E. coli* is a prokaryotic host useful particularly for cloning the polynucleotides of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

In addition to bacteria, other microbes, such as yeast, may also be used for expression. *Pichia pastoris* is a preferred host, with suitable vectors having expression control sequences, such as promoters, including 3-phosphoglycerate kinase or other glycolytic enzymes, and an origin of replication, termination sequences and the like as desired.

Mammalian tissue cell culture may also be used to express and produce the polypeptides of the present invention. Eukaryotic cells are actually preferred, because a number of suitable host cell lines capable of secreting intact immunoglobulins have been developed in the art, and include the CHO cell lines, various COS cell lines, HeLa cells, myeloma cell lines, transformed B-cells, human embryonic kidney cell lines, or hybridomas. Preferred cell lines are CHO and myeloma cell lines such as SP2/0 and NS0.

Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. Preferred polyadenylation sites include sequences derived from SV40 and bovine growth hormone.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Once expressed, the antibodies can be purified according to standard procedures, including ammonium sulfate precipitation, ion exchange, affinity (e.g. Protein A), reverse phase, hydrophobic interaction column chromatography, gel electrophoresis, and the like. Substantially pure immunoglobulins having at least about 90 to 95% purity are preferred, and 98 to 99% or more purity most preferred, for pharmaceutical uses. Once purified, partially or to homogeneity as desired, the polypeptides may then be used therapeutically or prophylactically, as directed herein.

Antibodies of the present invention are useful in therapeutic, prophylactic, diagnostic and research applications as described herein. An antibody of the invention may be used to diagnose a disorder or disease associated with the expression of human IL-23. In a similar manner, the antibody of the invention can be used in an assay to monitor IL-23 levels in a subject being tested for an IL-23-associated condition. Research applications include methods that utilize the antibody of the invention and a label to detect IL-23 in a sample, e.g., in a human body fluid or in a cell or tissue extract. Antibodies of the invention may by used with or without modification, and are labeled by covalent or non-covalent attachment of a detectable moiety. The detectable moiety can be any one that is capable of producing, either directly or indirectly, a detectable signal.

A variety of conventional protocols for measuring IL-23, including e.g., ELISAs, RIAs, and FACS, are known in the art and provide a basis for diagnosing altered or abnormal levels of IL-23 expression. Normal or standard expression values are established using any art known technique, e.g., by combining a sample comprising a IL-23 polypeptide with, e.g., antibodies under conditions suitable to form a antigen:antibody complex. The antibody is directly or indirectly labeled with a detectable substance to facilitate detection of the bound or unbound antibody. Suitable detectable substances include various enzymes, prosthetic groups, fluorescent materials, luminescent materials and radioactive materials.

As a matter of convenience, the antibody of the present invention can be provided in a kit, a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a blocking buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

This invention also relates to a method of treating humans experiencing an IL-23 mediated inflammatory disorder which comprises administering an effective dose of an antibody specific to the p19 subunit of human IL-23 to a patient in need thereof. The antibodies of the present invention bind to and neutralize IL-23. Various IL-23-mediated disorders include multiple sclerosis, rheumatoid arthritis (RA), graft versus host disease, psoriasis, Crohn's disease, other inflammatory bowel diseases, and cancer. Preferably, the IL-23 antibodies encompassed by the present invention are used to treat relapsing remitting multiple sclerosis, the most common form of multiple sclerosis.

The antibodies, or antigen binding portions thereof, of the present invention can be in the form of a composition comprising the antibody of the invention suspended in a pharmacologically acceptable diluent or excipient. These pharmaceutical compositions may be administered by any means known in the art that achieve the generally intended purpose to treat autoimmune diseases, preferably multiple sclerosis. The preferred route of administration is parenteral, defined herein as referring to modes of administration that include intravenous, intramuscular, intraperitoneal, intrasternal, subcutaneous, and intraarticular injection and infusion. More preferably, the route of administration is subcutaneous and is administered once weekly. The dosage administered will be dependent upon the age, health, and weight of the recipient, kind of concurrent treatment, if any, frequency of treatment, and the nature of the effect desired.

Compositions within the scope of the invention include all compositions wherein an antibodies or antigen binding portion is present in an amount that is effective to achieve the desired medical effect for treating multiple sclerosis. While individual needs may vary from one patient to another, the determination of the optimal ranges of effective amounts of all of the components is within the ability of the clinician of ordinary skill.

The pharmaceutical compositions for administration are designed to be appropriate for the selected mode of administration, and pharmaceutically acceptable excipients such as, buffers, surfactants, preservatives, solubilizing agents, isotonicity agents, stabilizing agents, carriers, and the like are used as appropriate. *Remington's Pharmaceutical Sciences*, Mack Publishing Co., Easton Pa., latest edition, incorporated herein by reference, provides a compendium of formulation techniques as are generally known to practitioners.

The concentration of the IL-23 antibody in formulations may be from as low as about 0.1% to as much as 15 or 20% by weight and will be selected primarily based on fluid volumes, viscosities, stability, and so forth, in accordance with the particular mode of administration selected. Preferred concentrations of the IL-23 antibody will generally be in the range of 1 to about 100 mg/mL. Preferably, 10 to about 50 mg/mL.

The formulation may include a buffer. Preferably the buffer is a citrate buffer or a phosphate buffer or a combination thereof. Generally, the pH of the formulation is between about 4 and about 8. Preferably, the pH is between about 5 and about 7.5. The pH of the formulation can be selected to balance antibody stability (chemical and physical) and comfort to the patient when administered. The formulation may also include a salt such as NaCl. In addition, the formulation may include a detergent to prevent aggregation and aid in maintaining stability.

The formulation may be sterile filtered after making the formulation, or otherwise made microbiologically acceptable. A preservative such as m-cresol or phenol, or a mixture thereof may be added to prevent microbial growth and contamination.

A typical composition for intravenous infusion could have a volume as much as 250 mL of fluid, such as sterile Ringer's solution, and 1-100 mg per mL, or more in antibody concentration. Therapeutic agents of the invention can be frozen or lyophilized for storage and reconstituted in a suitable sterile carrier prior to use. Lyophilization and reconstitution can lead to varying degrees of antibody activity loss (e.g., with conventional immunoglobulins, IgM antibodies tend to have greater activity loss than IgG antibodies). Dosages may have to be adjusted to compensate.

Although the foregoing methods appear to be the most convenient and most appropriate for administration of proteins such as humanized antibodies, by suitable adaptation, other techniques for administration, such as transdermal administration and oral administration may be employed provided proper formulation is designed. In addition, it may be desirable to employ controlled release formulations using biodegradable films and matrices, or osmotic mini-pumps, or delivery systems based on dextran beads, alginate, or collagen. In summary, formulations are available for administering the antibodies of the invention and may be chosen from a variety of options.

Typical dosage levels can be optimized using standard clinical techniques and will be dependent on the mode of administration and the condition of the patient. Generally, doses will be in the range of 10 µg/kg/month to 10 mg/kg/month.

In another aspect, the antibodies or antigen binding portions thereof of the present invention for use as a medicament for the treatment of autoimmune disease is contemplated.

In yet another aspect, an article of manufacture containing materials useful for the treatment or prevention of the disorders or conditions described above is provided. The article of manufacture comprises a container and a label. Suitable containers include, for example, bottles, vials, syringes, and test tubes. The containers may be formed from a variety of materials such as glass or plastic. The container holds a composition of an antibody of the invention which is effective for preventing or treating the disorder or condition and may have a sterile access port (for example the container may be an intravenous solution bag or a vial having a stopper pierceable by a hypodermic injection needle). The active agent in the composition is an anti-IL-23 antibody of the invention. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention is illustrated by the following examples that are not intended to be limiting in any way.

Example 1

IL-23 Inhibition Assay

A mouse splenocyte assay is used to determine inhibition of IL-23 activity based on the ability of IL-23 to stimulate IL-17 secretion from mouse spleen cells. The antibodies of the present invention are compared to MAb3A8 and to a commercially available murine monoclonal antibody, MAB1290 (R&D Systems).

The basic protocol is as follows. Spleens are removed from 1 BALB/c or C57BL/6 mice and the splenocytes are harvested and a single cell suspension is prepared. The splenocytes are washed and resuspended in complete RPMI (containing 1% non-essential amino acids, 1% sodium pyruvate, 2.5 mM HEPES, 1% L-glutamine, 0.00035% 2-mercaptoethanol, 1% Pen/Strep, 10% heat-inactivated FCS and 50 ng/mL human IL-2 (R and D Systems)). The splenocytes are then seeded at 500,000 cells/well in a 96-well culture plate in a volume of 100 microliters.

Human IL-23 (R and D Systems) at a concentration of 10 pM is preincubated with 3-fold serial dilutions of test antibodies over a range of 0.001 to 54 micrograms/mL. Incubation is performed in a separate assay plate at 37° C., 5% $CO_2$ for 90 minutes.

100 microliters of each pre-incubation sample is then added to the culture plate containing splenocytes and incubated for 48-72 hours at 37° C., 5% $CO_2$. A sandwich ELISA kit for mouse IL-23 (M1700, R and D Systems), is used to measure the amount of IL-23 in each culture supernatant. IC50 is the amount of antibody needed to neutralize 50% of the bioactivity of IL-23 on mouse splenocytes.

The $IC_{50}$ of MAb3A8 and the antibodies of the present invention compared to that of MAB1290 in the Murine Splenocyte Assay is shown in Table 3. The exemplified antibodies, MAbQF20 and MAbQF37, significantly neutralize the IL-23 stimulation of IL-17 secretion from mouse spleen cells having $IC_{50}$ values of less than 20 pM.

TABLE 3

$IC_{50}$ Measured in the Murine Splenocyte Assay

| SAMPLE | SEQ ID NO HCVR/LCVR | SEQ ID NO HCCR/LCCR | $IC_{50}$ pM |
|---|---|---|---|
| MAb3A8 | | | 4 |
| MAB1290 | | | 2800 |
| MAbQF20 | 48/57 | 62/63 | 2 |
| MAbQF37 | 52/57 | 62/63 | 2 |

Example 2

Neutralization of Human IL-23

Human IL-23 along with IL-2 injected into mice is able to stimulate mouse IL-17 production in spleen cells. This stimulation of IL-17 is blocked with neutralizing antibodies to the p19 subunit of IL-23 and is demonstrated in the following in vivo murine model with an ex vivo readout of IL-17 production.

C57BL/6 mice are primed with an injection of murine IL-2 (mIL-2), 22 hours prior to stimulation of the mice with mIL-2 plus human IL-23. Two hours prior to stimulation with mIL-2 and hIL-23, the mice are injected with either a high affinity humanized antibody of the present invention or an isotype matched (IgG4) control antibody.

The following groups are then set-up:

At Time=0, an i.p. injection of mIL-2 only (5 µg) or mIL-2 (5 µg) plus human IL-23 (10 µg)

At 7 hours, an i.p. injection of mIL-2 only (10 µg) or mIL-2 (10 µg) plus human IL-23 (10 µg)

At 23 hours, an i.p injection of mIL-2 only (5 µg) or mIL-2 (5 µg) plus human IL-23 (10 µg)

At 30 hours, the mice are sacrificed, the spleens removed and the splenocytes are harvested and a single cell suspension is prepared. The splenocytes are washed in complete RPMI (containing 1% non-essential amino acids, 1% sodium pyruvate, 2.5 mM HEPES, 1% L-glutamine, 0.00035% 2-mercaptoethanol, 1% Pen/Strep, 10% heat-inactivated fetal calf serum) and seeded at 200,000 cells/200 µl/well in a 96-well culture plate that is pre-coated with hamster anti-mouse CD3e antibody (5 µg/ml in PBS overnight at 4° C.). The 96-well plate is then incubated for 48-72 hours at 37° C., 5% $CO_2$.

A sandwich ELISA kit for mouse IL-17 (M1700, R and D Systems) is used to measure the amount of IL-17 in each culture supernatant. As shown in Table 4, MAbQF20 and MAbQF37 neutralize IL-23 and significantly block the stimulation of IL-17.

TABLE 4

| Antibody/Stimulation | IL-17 Level (pg/mL) Experiment 1 | IL-17 Level (pg/mL) Experiment 2 |
|---|---|---|
| Isotype control/IL-2/IL-23 | 4100 | 4500 |
| MAbQF20/IL-2/IL-23 | 1600 | 1500 |
| MAbQF37/IL-2/IL-23 | 1600 | 1700 |

Example 3

Binding Affinity

Affinities of MAb3A8 and antibodies of the present invention are determined using BIAcore measurements (Table 3). BIAcore™ is an automated biosensor system that measures molecular interactions. (Karlsson, et al. (1991) *J. Immunol. Methods* 145: 229-240). In these experiments antibody is captured to a surface at low density on a BIAcore™ chip. Ethyl-dimethylaminopropyl-carbodiimide (EDC) is used to couple reactive amino groups to protein A to a flow cell of a carboxy-methyl (CM5) BIAcore™ sensor chip. Protein A is diluted in sodium acetate buffer, pH 4.5, and immobilized on a flow cell of a CM5 chip using EDC to yield 1000 response units. Unreacted sites are blocked with ethanolamine. A flow rate of 60 μl/min is used. Multiple binding/elution cycles are performed by injection a 10 μl solution of 2 μg/mL of the antibodies of the present invention. followed by human IL-23 at decreasing concentrations for each cycle (e.g. 1500, 750, 375, 188, 94, 47, 23.5, 12, and 0 picomolar). Elution is performed with glycine-HCl, pH 1.5. BIAevaluation™ is used to analyze the kinetic data.

The $K_D$ of MAb3A8 is compared to antibodies of the present invention and to the commercially available anti-IL23 neutralizing monoclonal antibody MAb1290 (Table 5). The results indicate that the exemplified antibodies, MAbQF20 and MAbQF37, have an affinity constant 2-6 times less than that of MAb3A8 having $K_D$ values from less than about 160 pM.

TABLE 5

Binding properties of anti-IL-23 antibodies to human IL-23 determined by BIAcore (HBS-EP buffer, pH 7.4 at 25° C.)

| ANTIBODY | $k_{on}$ (M$^{-1}$s$^{-1}$) | $k_{off}$ (s$^{-1}$) | $K_D$ (pM) |
|---|---|---|---|
| MAb3A8 | $3.0 \times 10^5$ | $9.12 \times 10^{-5}$ | 300 |
| MAb1290* | $3.68 \times 10^4$ | $7.68 \times 10^{-4}$ | 21,400 |
| MAbQF20 | $1.55 \times 10^6$ | $1.15 \times 10^{-4}$ | 74 |
| MAbQF37 | $1.55 \times 10^6$ | $1.53 \times 10^{-4}$ | 98 |

*anti-human IL-23 monoclonal antibody, murine (R&D Systems)

Example 4

Epitope Mapping of IL-23

The epitope of the p19 subunit of IL-23 recognized by the humanized antibodies of the present invention is comprised within amino acid residues 129 to 159 of SEQ ID NO:60. The epitope is determined by Amide Deuterium Exchange Mass Spectrometry (DXMS).

DXMS is useful for determining the protein-protein interactions between the p19 subunit of IL-23 and the humanized antibodies of the present invention. A Fab fragment of MAb3A8 is used as model binding fragment. Several epitopes are identified with this procedure and include in addition to residues 129 to 159 of SEQ ID NO: 60, residues 129-152; 151-159; and 134-152, with all residue positions based on SEQ ID NO: 60.

A standard ELISA competition assay is utilized to determine that the humanized antibodies of the present invention bind the same epitope as MAb3A8. The candidate humanized antibodies are assayed with biotinylated MAb3A8 in a concentration-dependent manner. A concentration-dependent competition indicates that the competing antibodies bind the same epitope on mature IL-23. Thus, the humanized antibodies of the present invention bind the above identified epitope of the p19 subunit of IL-23 and neutralize the activity of IL-23 and thereby are useful in treating inflammatory disorders associated with IL-23 expression such as autoimmune disease, preferably multiple sclerosis.

Example 5

EAE Model for Multiple Sclerosis

EAE is a CD4+ T cell-mediated demyelinating disease of the central nervous system (CNS) that serves as a model for MS in humans. The pathogenic mechanisms of EAE development include antigen-specific T cell activation and Th1 differentiation followed by T cell and macrophage infiltration into the CNS. IL-23 stimulates secretion of IL-17 from T cells and IL-17 contributes to the pathology of multiple sclerosis (MS). Elevated levels of IL-23 have been identified in the sera of MS patients and microarray analysis of MS lesions of human patients has demonstrated an increase of IL-17 (Lock, et al. *Nat. Med.* 8:500-508, 2002). IL-17 mRNA-expressing mononuclear cells (MNC) in blood and cerebrospinal fluid are significantly elevated in number in MS patients and higher numbers of IL-17 mRNA-expressing blood MNC were detected during MS clinical exacerbation compared to remission (Matusevicius, et al. *Multiple Sclerosis,* 5:1-1-104, 1999).

The example described here demonstrates the effect of an anti-IL-23 antibody in the relapsing-remitting EAE model, wherein an anti-murine IL-23 antibody inhibits the secretion of IL-17 from T-cells and consequently, reduces the EAE score in the active EAE model. For disease induction, 8-9 week old SJL/J mice are injected subcutaneously at two spots on the flank on day 0 with 100 μl of Complete Freund's Adjuvant (CFA) containing 50 μg PLP 139-151 and 200 μg *Mycobacterium tuberculosis* H37 RA. On the day of first remission (day 23-26), the mice are randomly divided into three treatment groups: (i) vehicle (PBS), (ii) IgG$_1$ isotype control antibody, 10 mg/kg, and, (iii) murine anti-murine IL-23 monoclonal IgG$_1$ antibody, 10 mg/kg. The animals are injected with 0.2 ml, i.p., beginning on the day of first remission and then weekly for 6 weeks.

Mice are scored from day 7 through day 60 for levels of paralysis. Mice are sacrificed one week after the final treatment. Clinical signs of disease develop about day 12 to day 15 with peak disease occurring about day 17 to day 22. Individual animals are subjectively scored by at least 2 scorers independently and blinded to the identity of treatment groups according to clinical CNS disease severity. Grade 0 is normal; Grade 0.5, Distal limp or spastic tail; Grade 1 Complete limp tail; Grade 1.5 Limp tail and hind limb weakness; Grade 2.0 unilateral partial hind limb paralysis; Grade 2.5 Bilateral partial-hind-limb paralysis; Grade 3.0 Complete bilateral hind-limb paralysis; Grade 3.5 Complete hind limb and unilateral partial-forelimb paralysis; Grade 4.0 Total paralysis of fore and hind limbs; Grade 5.0 Moribund or death. The IL-23 antibody treatment group has significantly lower disease scores as compared to the isotype control group.

The spleens of the mice in each treatment group are removed and individual, single cell suspensions of the splenocytes are made. The splenocytes are cultured for 2 days in the presence of PLP (the peptide used to induce EAE onset, thus a re-stimulation of the immune cell population in an ex-vivo setting). After 2 days the culture supernatants are assayed for the concentration of 22 cytokines/chemokines (utilizing a standardized kit by Linco, Inc.). The culture supernatants from the group treated with the isotype control MAb have an IL-17 concentration of about 450 pg/ml whereas the culture supernatants from the group treated with the anti-IL-23 MAb have an IL-17 concentration of about 175 pg/ml. Thus, a significant reduction (p<0.002) in the concentration of mouse IL-17 is observed in the group treated with the anti-IL-23 MAb.

We claim:

1. A humanized antibody that specifically binds to the p19 subunit of human IL-23 and comprises a light chain variable region (LCVR) polypeptide and a heavy chain variable region (HCVR) polypeptide selected from the group consisting of:
   (a) a LCVR as shown in SEQ ID NO:57 and a HCVR as shown in SEQ ID NO: 47;
   (b) a LCVR as shown in SEQ ID NO:57, and a HCVR as shown in SEQ ID NO: 48;
   (c) a LCVR as shown in SEQ ID NO:57 and a HCVR as shown in SEQ ID NO: 49;
   (d) a LCVR as shown in SEQ ID NO:57 and a HCVR as shown in SEQ ID NO: 51;
   (e) a LCVR as shown in SEQ ID NO:57 and a HCVR as shown in SEQ ID NO: 52;
   (f) a LCVR as shown in SEQ ID NO:57 and a HCVR as shown in SEQ ID NO: 53, and,
   (g) a LCVR as shown in SEQ ID NO:57 and a HCVR as shown in SEQ ID NO: 55.

2. A humanized antibody that specifically binds to the p19 subunit of human IL-23 and comprises a light chain variable region (LCVR) polypeptide as shown in SEQ ID NO:57, a heavy chain variable region (HCVR) polypeptide as shown in SEQ ID NO:52, a light chain constant region (LCCR) as shown in SEQ ID NO:63 and a heavy chain constant region (HCCR) as shown in SEQ ID NO:62.

3. A humanized antibody that specifically binds to the p19 subunit of human IL-23 and comprises a light chain variable region (LCVR) polypeptide as shown in SEQ ID NO:57, a heavy chain variable region (HCVR) polypeptide as shown in SEQ ID NO:48, a light chain constant region (LCCR) as shown in SEQ ID NO:63, and a heavy chain constant region (HCCR) as shown in SEQ ID NO:62.

* * * * *